US009924915B2

(12) United States Patent
Kodaira

(10) Patent No.: US 9,924,915 B2
(45) Date of Patent: Mar. 27, 2018

(54) X-RAY CT APPARATUS

(71) Applicant: Toshiba Medical Systems Corporation, Otawara (JP)

(72) Inventor: Yasuo Kodaira, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 522 days.

(21) Appl. No.: 14/235,924

(22) PCT Filed: Feb. 21, 2013

(86) PCT No.: PCT/JP2013/054267
§ 371 (c)(1),
(2) Date: Jan. 29, 2014

(87) PCT Pub. No.: WO2013/125616
PCT Pub. Date: Aug. 29, 2013

(65) Prior Publication Data
US 2014/0169531 A1    Jun. 19, 2014

(30) Foreign Application Priority Data
Feb. 22, 2012   (JP) ................................. 2012-036222

(51) Int. Cl.
*A61B 6/00* (2006.01)
*H05G 1/02* (2006.01)
(Continued)

(52) U.S. Cl.
CPC ............ *A61B 6/4488* (2013.01); *F24F 7/065* (2013.01); *F24F 13/081* (2013.01); *F24F 13/24* (2013.01);
(Continued)

(58) Field of Classification Search
CPC ........... A61B 6/00; A61B 6/44; A61B 6/4411; A61B 6/4488; H05G 1/00; H05G 1/02;
(Continued)

(56) References Cited

U.S. PATENT DOCUMENTS 3,322,233 A * 5/1967 McCluer ................... E04B 1/84
181/290
6,608,429 B1 * 8/2003 Snyder ..................... H05G 1/04
313/36
(Continued)

FOREIGN PATENT DOCUMENTS

CN   101061955 A   10/2007
CN   101574265 A   11/2009
(Continued)

OTHER PUBLICATIONS

International Search Report dated Jun. 4, 2013 in PCT/JP13/054267 Filed Feb. 21, 2013.
(Continued)

*Primary Examiner* — Anastasia Midkiff
(74) *Attorney, Agent, or Firm* — Oblon, McClelland, Maier & Neustadt, L.L.P.

(57) ABSTRACT

In an X-ray CT apparatus, an annular rotating body includes an X-ray tube and an opening portion accommodating a radiator that discharges heat from the X-ray tube and into which a bed can be inserted. A stand includes a frame disposed in a rear portion of the annular rotating body, and supports the annular rotating body to be rotatable about an axis. A cover which covers the annular rotating body and the stand includes an exhaust port. A cooling mechanism, disposed at a position away from a position of the exhaust port along a circumferential direction of the annular rotating body between an outer circumferential surface of the annular rotating body and cover, includes a fan disposed at the stand. A duct receives exhaust air from the fan at a rear position of (Continued)

the fan between the frame and cover, and leads from the fan to the exhaust port.

19 Claims, 15 Drawing Sheets

(51) Int. Cl.
*F24F 7/06* (2006.01)
*F24F 13/08* (2006.01)
*F24F 13/24* (2006.01)
*A61B 6/03* (2006.01)

(52) U.S. Cl.
CPC ......... *A61B 6/035* (2013.01); *F24F 2013/242* (2013.01); *F24F 2013/245* (2013.01); *H05G 1/02* (2013.01)

(58) Field of Classification Search
CPC ...... H05G 1/04; F24F 7/00; F24F 7/04; F24F 7/06; F24F 7/065; F24F 7/08; F24F 7/10; F24F 2007/001; F24F 2013/0608; F24F 2013/242; F24F 2013/245; F24F 2013/247; F24F 13/00; F24F 13/02; F24F 13/0209; F24F 13/0245; F24F 13/0254; F24F 13/0281; F24F 13/06; F24F 13/0604; F24F 13/08; F24F 13/081; F24F 13/24; F24F 13/32
See application file for complete search history.

(56) References Cited

U.S. PATENT DOCUMENTS

| | | | |
|---|---|---|---|
| 7,889,837 B2 | 2/2011 | Takamatsu et al. | |
| 2004/0109538 A1* | 6/2004 | McCarthy, Jr. ........ | A61B 6/035 378/141 |
| 2004/0228450 A1* | 11/2004 | Mueller ............... | A61B 6/4488 378/199 |
| 2004/0240619 A1* | 12/2004 | Kendall ................ | H05G 1/025 378/141 |
| 2005/0287008 A1* | 12/2005 | Lacey .................. | F04D 27/004 417/32 |
| 2006/0215808 A1* | 9/2006 | Lacey .................. | A61B 6/4488 378/19 |
| 2009/0232281 A1 | 9/2009 | Jimbo et al. | |
| 2013/0200896 A1* | 8/2013 | Maciejewski .......... | G01R 33/28 324/318 |

FOREIGN PATENT DOCUMENTS

| | | |
|---|---|---|
| JP | 2009-219619 | 10/2009 |
| JP | 2009-268830 | 11/2009 |
| JP | 2010-227382 | 10/2010 |

OTHER PUBLICATIONS

Combined Office Action and Search Report dated Aug. 5, 2015 in Chinese Patent application No. 201380003147.X (with English translation of category of cited documents).

* cited by examiner

X-RAY CT APPARATUS

TECHNICAL FIELD

The embodiments of the present invention relate to an X-ray CT apparatus.

BACKGROUND ART

Conventionally, X-ray CT apparatuses detect X-rays, which are irradiated from an X-ray tube and passed through a subject, and reconstruct an image based on a result of the detection to obtain an X-ray tomographic image.

An X-ray tube is provided inside an annular rotator, and periphery of the annular rotator is covered with a cover. A space is formed between the outer circumferential surface of the annular rotator and the inner surface of the cover.

A cooler is provided in order to effectively exhaust the heat generated from the X-ray tube. In addition to the space, the cooler has a radiator, a vent hole, an exhaust fan, and an exhaust port, for example.

The radiator is arranged in vicinity of the X-ray tube. The vent hole which leads to the space is arranged in vicinity of the radiator. The space is provided with the exhaust port which leads to the outside air. An exhaust fan is provided between the exhaust port and the vent hole. High temperature air radiated from the radiator is passed through the vent hole and the exhaust fan causes the high temperature air to be exhausted to the outside via the exhaust port (Patent Document 1) (Japanese Unexamined Patent Application Publication No. 2009-219619).

Further, as another example of the cooler, a duct for exhausting heat is provided. The duct for exhausting heat is formed so as to extend along the outer circumference of a rotating part, ensuring a length of the duct long enough to attenuate noise energy which is generated in a component and propagated inside the duct (Patent Document 2) (Japanese Unexamined Patent Application Publication No. 2010-227382).

PRIOR ART DOCUMENT

Patent Documents

[Patent Document 1] Japanese Unexamined Patent Application Publication No. 2009-219619
[Patent Document 2] Japanese Unexamined Patent Application Publication No. 2010-227382

SUMMARY OF THE INVENTION

Problems to be Solved by the Invention

However, according to the technique in Patent Document 1 (Japanese Unexamined Patent Application Publication No. 2009-219619), since the exhaust fan is arranged to close to the exhaust port, the noise generated from the exhaust fan is not reduced but leaked from the exhaust port to the outside. Also, according to the technique in Patent Document 2 (Japanese Unexamined Patent Application Publication No. 2010-227382), since the duct for exhausting heat is extended along the outer circumference of the rotating part, there was a problem such that the X-ray CT apparatus became large in size.

The present embodiments are intended to solve the above-described problems, and the object is to provide an X-ray CT apparatus being able to reduce noise without becoming large in size.

Means of Solving the Problems

In order to solve the above-described problems, the X-ray CT apparatus of the present embodiments comprises an annular rotator, a gantry, a cover, coolers, and a duct, wherein an X-ray tube and radiators for exhausting the heat therefrom are installed inside the annular rotator. The annular rotator comprises an aperture to which a couch is insertable from the front to the center of the rotator. The gantry comprises a frame arranged rearward of the annular rotator, and supports the annular rotator to allow the annular rotator to rotate around an axis. The cover covers the annular rotator and the gantry, and is provided with exhaust ports. The coolers are arranged along the circumferential direction of the annular rotator at a position between the outer peripheral surface of the annular rotator and the cover, away from the positions of the exhaust ports. The coolers comprise one or a plurality of fan set on the gantry. The duct is arranged between the frame and the cover, and receives the exhaust air from the fan at the rearward of the fans, and passes the air therefrom to the exhaust ports. The fan comprises a fan axis inclining rearward with respect to an irradiation direction around the axis, and sends the heat exhausted by rotating around the fan axis to the duct.

MODES FOR CARRYING OUT THE INVENTION

Figure 1:
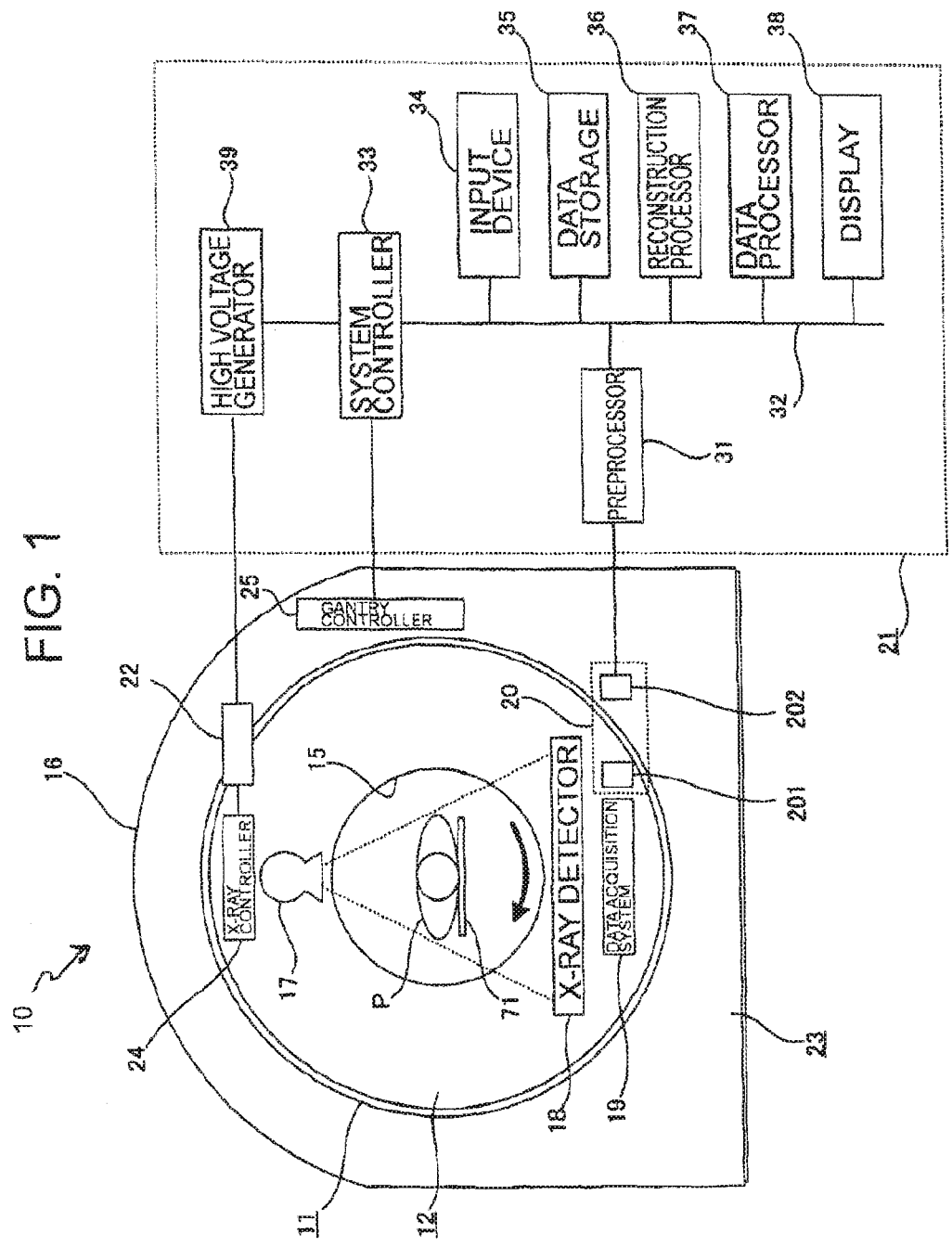
FIG. 1 is a block diagram of an X-ray CT apparatus according to a first embodiment.

[First Embodiment]
An X-ray CT apparatus according to a first embodiment is described with reference to FIGS. 1 to 3. FIG. 1 is a block diagram of the X-ray CT apparatus, FIG. 2 is a conceptual diagram of the inside of the X-ray apparatus as seen from the front, and FIG. 3 is a cross-sectional view taken along the line III-III of FIG. 2.

Figure 2:
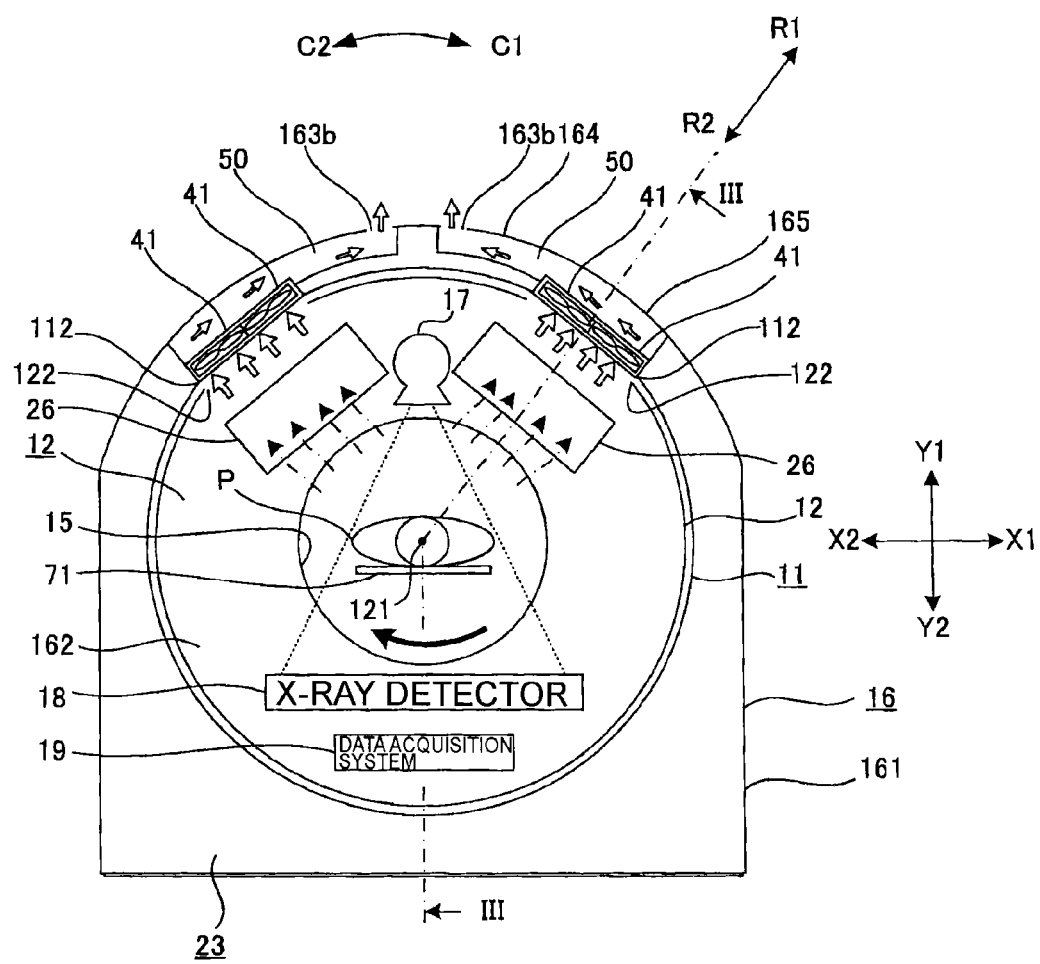
FIG. 2 is a conceptual diagram of the inside of the X-ray apparatus as seen from the front.
Figure 3:
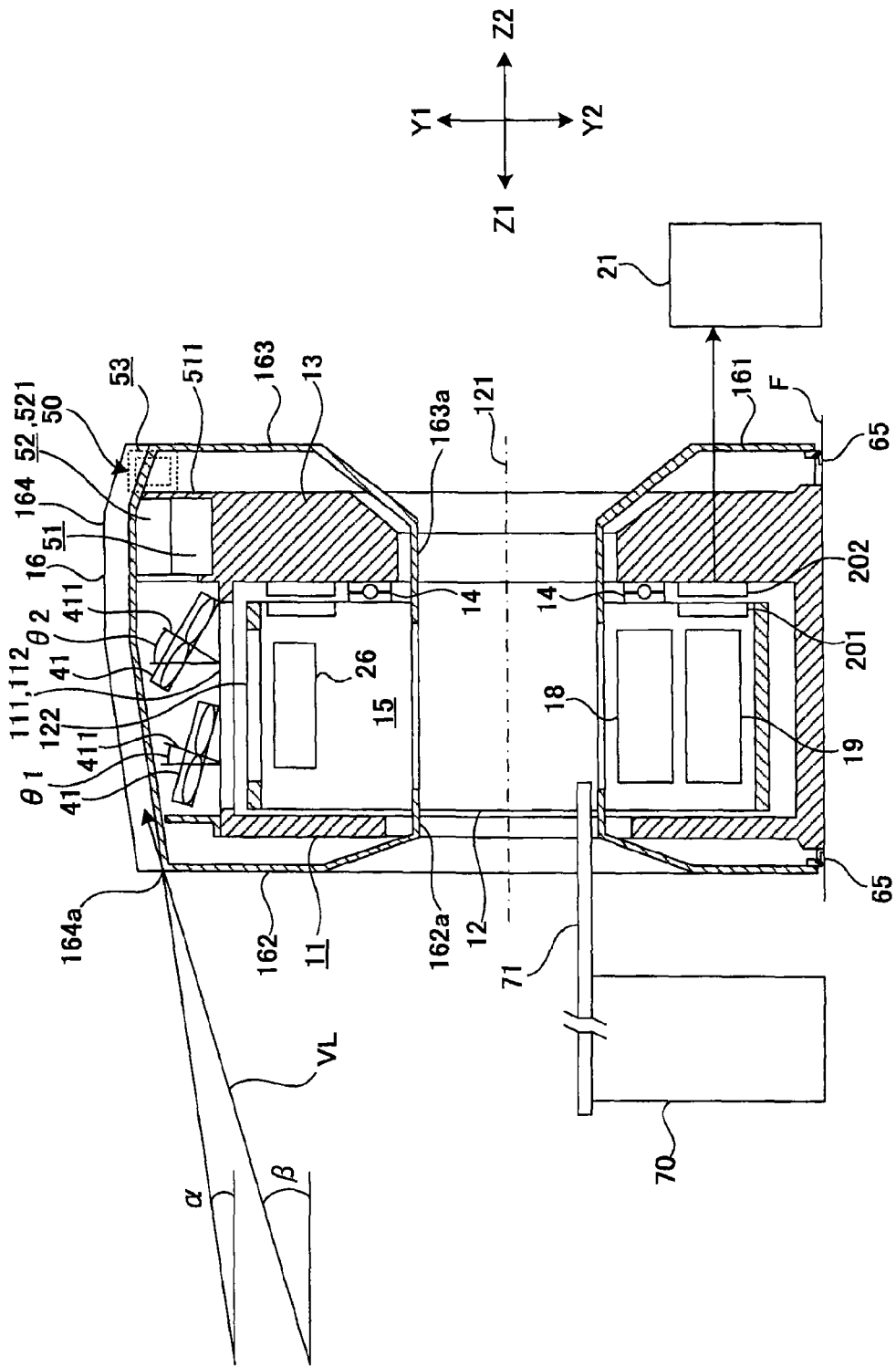
FIG. 3 is a cross-sectional view taken along the line III-III of FIG. 2.

In FIGS. 1 to 3, as the X-ray CT apparatus, an example of an X-ray CT apparatus for medical diagnosis is illustrated.

An X-ray CT apparatus 10 comprises a gantry 11, an annular rotator 12, rotating mechanisms 14, a cover 16, coolers 40, and a duct 50.

Inside the gantry 11, the annular rotator 12 and the rotating mechanisms 14 are provided. The annular rotator 12 is rotated by the rotating mechanisms 14.

Inside the annular 12, an X-ray tube 17 and an X-ray detector 18 are provided. At the center of the gantry 11 and the annular rotator 12, an aperture 15 is provided in order to insert a subject P placed on a top 71 of a couch 70 from the front of the rotator.

The cover 16 is formed to cover the gantry 11 and the annular rotator 12. The detail description of the cover 16 will be described later.

The X-ray tube 17 and the X-ray detector 18 are arranged facing each other around the aperture 15. X-rays are irradiated from the X-ray tube 17 to the subject P. The X-rays passing through the subject P are detected and then converted into an electric signal by the X-ray detector 18. The electric signal is amplified and converted into digital data by a data acquisition system (DAS) 19. The detail description of a mechanism to cool the X-ray tube 17 (cooling mechanism) will be described later.

The X-ray detector 18 includes multiple detection element arrays configuring by, for example, scintillator arrays, and photodiode arrays, and the arrays are arrayed along an arc around a focus point of the X-ray tube 17. Further, the digital data (projection data) from the DAS 19 is transmitted to a console 21 via a data transmitter 20.

The data transmitter 20 transmits the projection data from the annular rotator 12 to the console 21 in a non-contact manner, comprises a sender 201 provided on the annular rotator 12 side and a receiver 202 provided on a fixed part of the gantry 11, and supplies the data received by the receiver 202 to the console 21. Further, the sender 201 is installed to an annular rotator, and the receiver 202 is installed to an annular fixed part.

Furthermore, a slip ring 22 and an X-ray controller 24 are provided to the annular rotator 12, and a gantry controller 25 is provided to a fixed part 23.

The console 21 forms a computer system, and the projection data from the data transmitter 20 is supplied to a preprocessor 31. The preprocessor 31 implements preprocessing, such as data correction, on the projection data, and outputs the processed data to a bus line 32.

The bus line 32 is connected to a system controller 33, an input device 34, a data storage 35, a reconstruction processor 36, a data processor 37, a display 38, and the like, and the system controller 33 is connected to a high voltage generator 39.

The system controller 33 functions as a host controller, and controls operations of each unit of the console 21, as well as controlling the gantry controller 25 and the high voltage generator 39. The data storage 35 stores data, such as tomographic images, and the reconstruction processor 36 reconstructs three-dimensional image data from projection data. The data processor 37 processes the stored image data in the data storage 35 and the reconstructed image data. The display 38 displays the data obtained by image data processing, and the like.

The input device 34 includes a keyboard, a mouse, and the like, is operated by a user (doctor, operator, and the like), and implements various setting for data processing. The input device 34 is also inputs various information such as states of the subject and examination methods.

The high voltage generator 39 controls the X-ray controller 24 via the slip ring 22, and supplies electricity to the X-ray tube 17 to provide the required power (tube voltage, tube current) for X-ray irradiation. The X-ray tube 17 generates beam X-rays spreading in two directions including a slice direction parallel to the rostrocaudal direction of the subject P and a channel direction orthogonal thereto. The spreading angle of the beam X-rays in the slice direction may be referred to as a cone angle, and the spreading angle thereof in the channel direction may be referred to as a fan angle.

[Cover]

Hereinabove, it has been described the fundamental construction of the X-ray CT apparatus.

Figure 4:
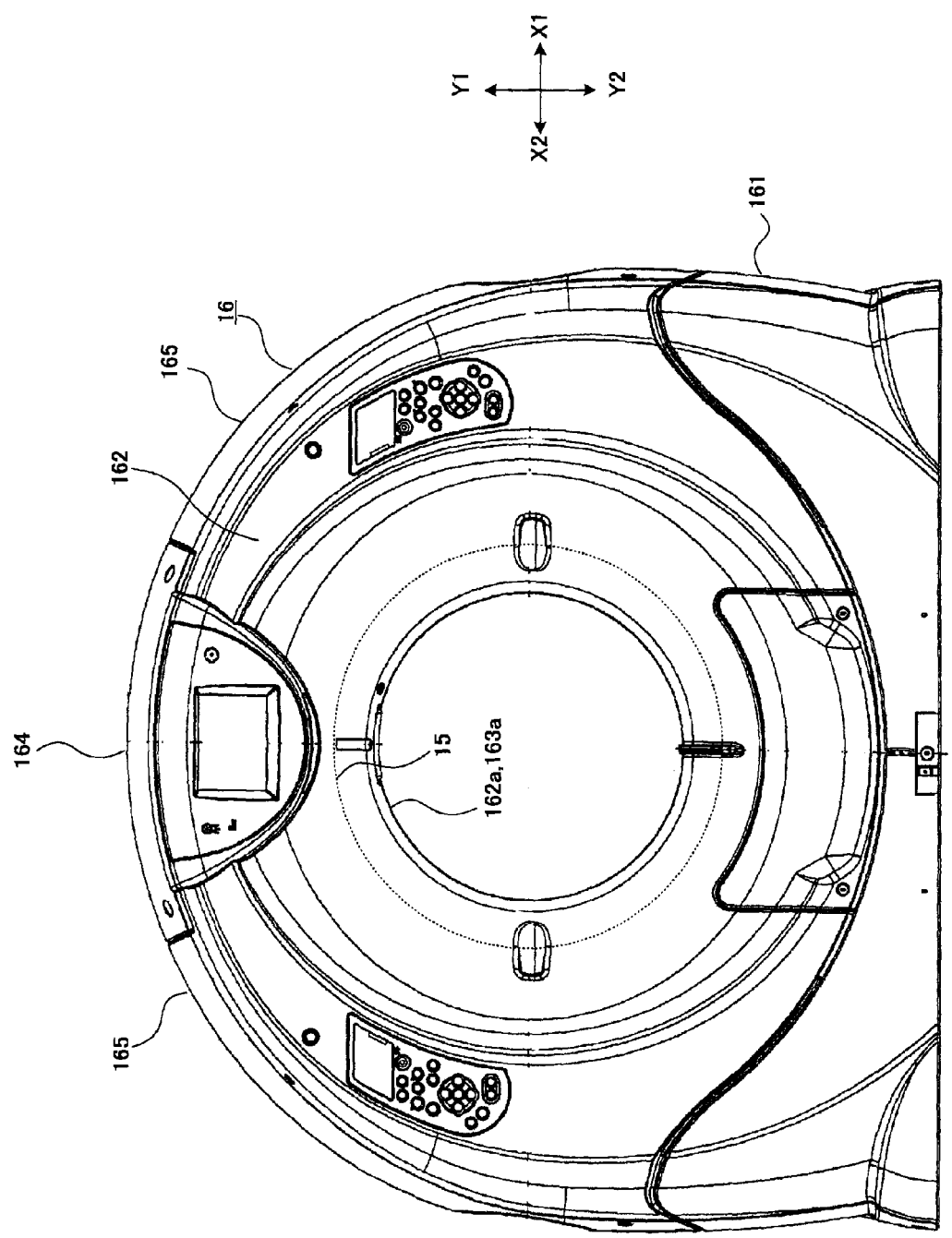
FIG. 4 is an elevation view of the X-ray CT apparatus.
Figure 5:
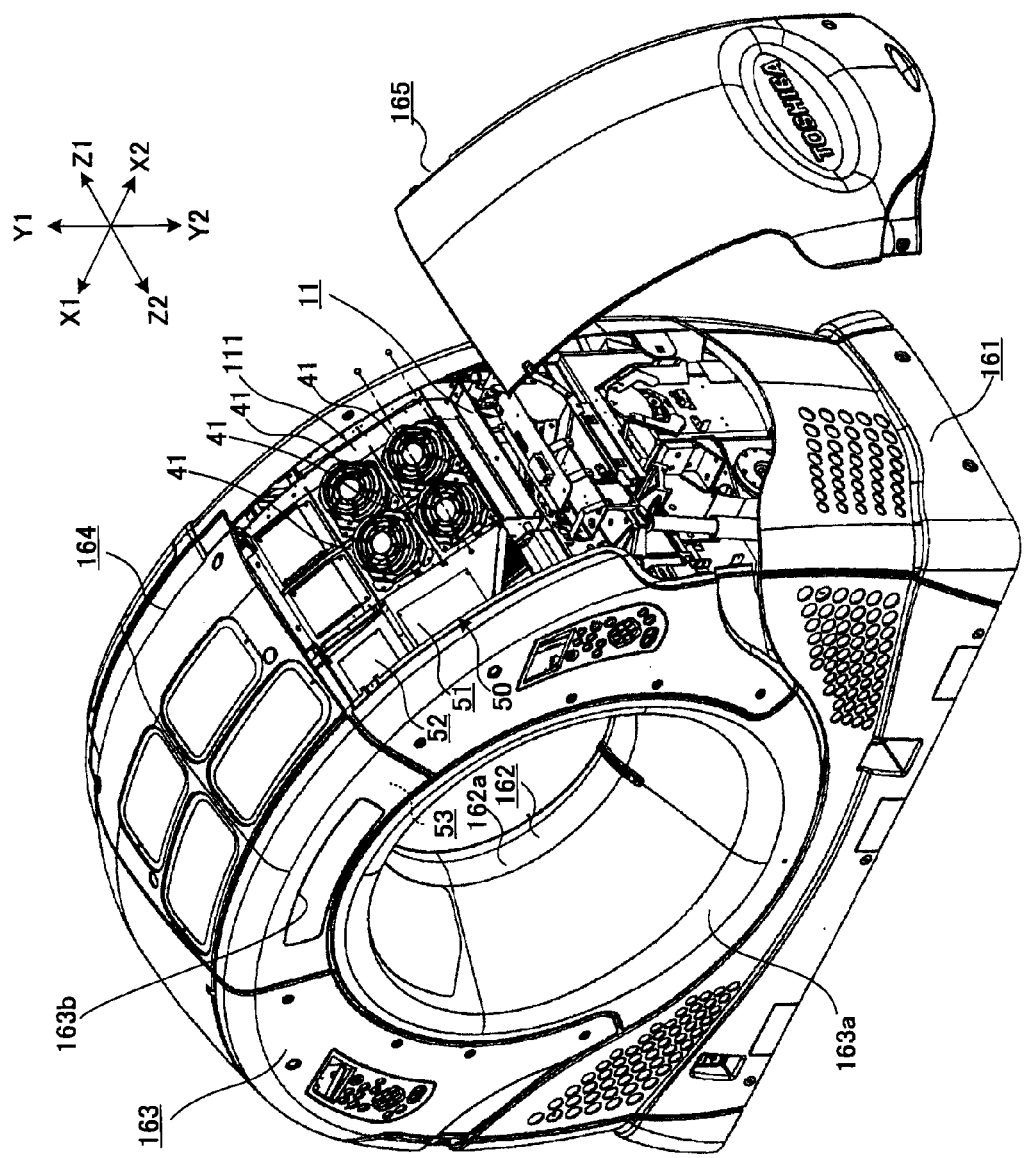
FIG. 5 is a perspective view of the X-ray CT apparatus as seen from a diagonally backward thereof.
Figure 6:
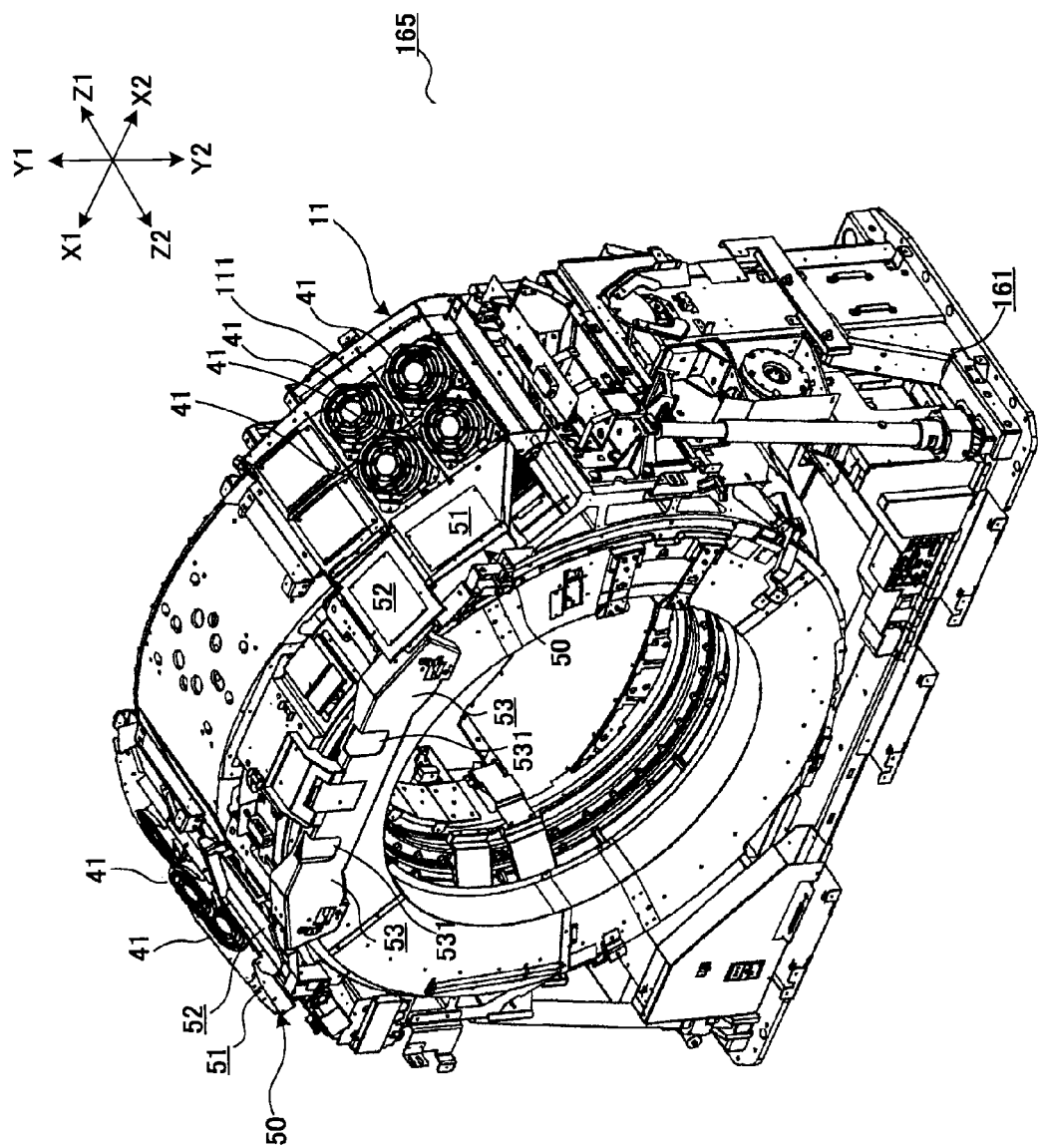
FIG. 6 is a perspective view of the inside of the X-ray CT apparatus as seen from a diagonally backward thereof.

Next, a detail description of the cover 16 is now described with reference to FIGS. 2 to 6. FIG. 4 is an elevation view of the X-ray CT apparatus, FIG. 5 is a perspective view of the X-ray CT apparatus as seen from a diagonally backward thereof, and FIG. 6 is a perspective view of the inside of the X-ray CT apparatus as seen from a diagonally backward thereof.

Here, parts of the gantry 11 arranged in the front side, rear side, both sides, upper side, and lower side of the annular rotator 12 may be referred to as a front surface, rear surface, side surfaces, ceiling part, and bottom part, respectively. Further, a longitudinal direction (sides direction), a vertical direction (height direction), and a rostrocaudal direction (front-rear direction) may be referred to as an X-axis direction, Y-axis direction, and Z-axis direction, respectively. Furthermore, the rear surface of the gantry 11 may be referred to as a frame 13.

In addition, in FIGS. 2 to 5, the front side and the rear side of the annular rotator 12 are denoted as Z1 and Z2, respectively, the right side and left side thereof are denoted as X1 and X2, respectively, and the upper side and lower side thereof are denoted as Y1 and Y2, respectively. Further, the circumference direction, clockwise direction, and anti-clockwise direction of the annular rotator 12 are denoted as C direction, C1 direction, and C2 direction, respectively. Furthermore, the direction to which X-rays are irradiated around a body axis 121 (irradiation direction) is denoted as R1, and the opposite direction of R1 (centripetal direction) is denoted as R2.

As shown in FIGS. 3 to 6, the cover 16 comprises a bottom cover 161 covering the bottom part of the gantry 11, a front cover 162 covering the front surface thereof, a rear cover 163 covering the rear surface thereof, a ceiling cover 164 covering the ceiling part thereof, and side covers 165 covering the side surfaces thereof.

The front cover 162 has a cylinder-opening front part 162a. The cylinder-opening front part 162a is formed in a cylindrical shape, and fitted from front to the aperture 15 to cover an approximately front half of the aperture 15 from the Z-axis direction (rostrocaudal direction).

The rear cover 163 has a cylinder-opening rear part 163a. The cylinder-opening rear part 163a is formed in a cylindrical shape, and fitted from rear to the aperture 15 to cover an approximately rear half of the aperture 15 from the Z-axis direction.

On the rear cover 163, exhaust ports 163b are arranged in order to exhaust heat from radiators 26, which will be described later, to the outside of the cover 16. The exhaust ports 163b are arranged at positions of 12 o'clock shown in FIG. 2 and FIG. 5. Since the heat from the radiators 26 rises inside the cover 16, it makes it possible to exhaust the heat effectively from the exhaust ports 163b arranged on the upper part of the rear cover 163. The noise generated from the inside of the cover 16, which is transmitted to the front side of the X-ray CT apparatus through the exhaust ports

163b, is reduced comparing to the case when the exhaust ports 163b are arranged at the front surface of either the front cover 162 or the bottom cover 161.

In order to exhaust the heat from the radiators 26 effectively, the exhaust ports 163b may be arranged on the upper part of the cover 16. For example, the exhaust ports 163b may be arranged on the ceiling cover 164.

Some parts of the duct 50, which will be described later, are covered with the rear cover 163. Further, fans 41 and other parts of the duct 50, which will be described later, are covered with the side covers 165. The fan 41 and the other parts of the duct 50 may be covered with other cover 16, for example, the ceiling cover 164.

[Cooling Mechanism]

Next, cooling mechanisms to cool the X-ray tube 17 are described with reference to FIG. 1 to FIG. 3, FIG. 5 and FIG. 6.

As shown in FIG. 2, two cooling mechanisms are symmetrically arranged with respect to one X-ray tube 17. The two cooling mechanisms have the same configurations.

The cooling mechanisms exhaust the heat from the X-ray tube 17 to the outside of the X-ray CT apparatus via the exhaust ports 163b, and comprise the radiators 26, the coolers 40 and the duct 50.

(Radiator)

As shown FIG. 2, the radiators 26 are symmetrically arranged in the X-axis direction around the X-ray tube 17. When the X-ray tube 17 is arranged at the position of 12 o'clock shown in FIG. 2, the radiators 26 are arranged at the positions of 1 o'clock and 11 o'clock shown in FIG. 2, respectively. In the outer circumference of the annular rotator 12, vent holes 122 are provided at the positions corresponding to the radiators 26 in a radiation direction (R1 direction). The vent holes 122 ventilate between the inside and outside (inside of the gantry 11) of the annular rotator 12.

(Cooler)

Next, the coolers 40 are described with reference to FIG. 2, FIG. 3, and FIGS. 5 to 8. FIG. 2 shows the coolers 40 arranged at the positions of 1 o'clock and 11 o'clock, respectively, and FIG. 5 shows the cooler 40 arranged at the position of 1 o'clock.

When the annular rotator 12 is rotated such that the position of the X-ray tube 17 corresponds to the positions of the exhaust ports 163b (rotating position represented at 12 o'clock in FIG. 2 and FIG. 5), the two coolers 40 are arranged at the positions corresponding to the positions of the two radiators 26 in the radiating direction, respectively.

Figure 7:
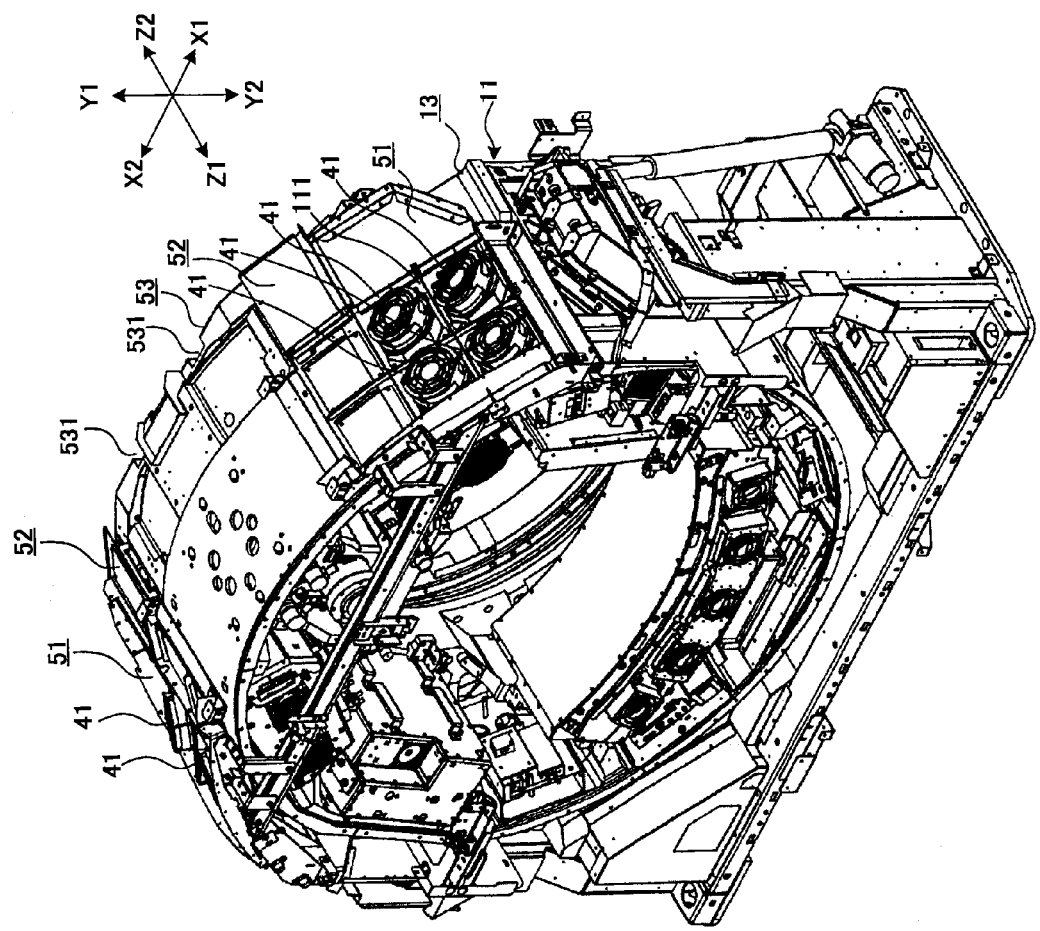
FIG. 7 is a perspective view of the inside of the X-ray CT apparatus as seen from a diagonally frontward thereof
Figure 8:
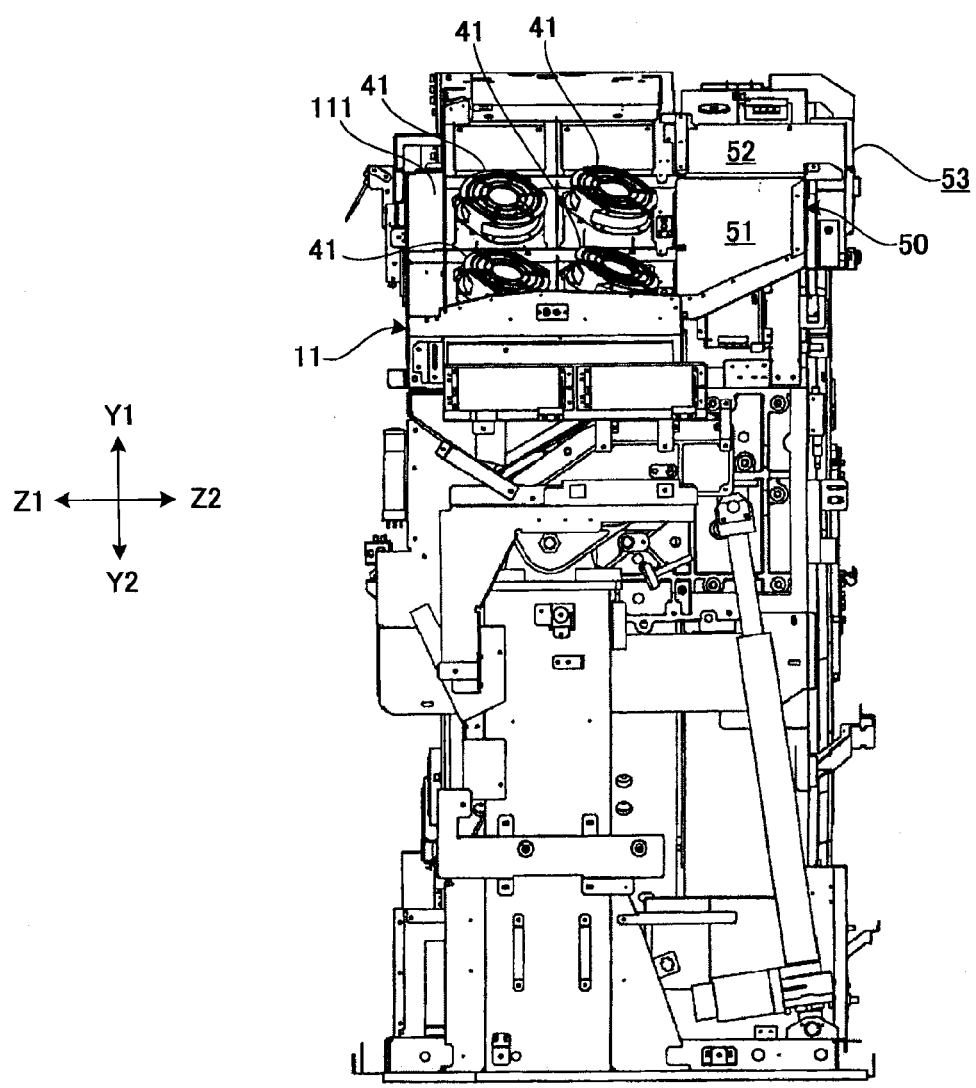
FIG. 8 is a side view of the inside of the X-ray CT apparatus.

FIG. 7 is a perspective view of the inside of the X-ray CT apparatus as seen from a diagonally frontward thereof, and FIG. 8 is a side view of the inside of the X-ray CT apparatus.

As shown in FIGS. 5 to 8, the cooler 40 comprises four fans 41. The four fans 41 are arranged in a matrix-form in the front-rear direction and the circumferential direction. Hereinafter, among those four fans, the two fans 41 arranged in the front-rear direction are described as a representative, and the description of the other two fans 41 arranged in the front-rear direction is omitted.

The fans 41 are arranged at positions, between the outer circumference surface of the annular rotator 12 and the cover 16 and separating from the position of the exhaust ports 163b, along the circumferential direction, and set on the ceiling part of the gantry 11. Since the exhaust ports 163b are provided at the positions of 12 o'clock, the fans 41 are arranged at the positions of 1 o'clock separating from the position of 12 o'clock in the a clockwise direction (C1 direction), and at the positions of 11 o'clock separating from the position of 12 o'clock in the an anticlockwise direction (C2 direction), respectively.

On each of parts (fan setting part) 111 of the ceiling part of the gantry 11 at which the fans 41 are provided, a communication port 112 is provided at the position corresponding to the radiator 26 in the radiation direction. The communication port 112 ventilates between the inside and the outside of the gantry 11.

Therefore, the communication port 112 of the gantry 11 and the vent hole 122 of the annular rotator 12 are provided at the positions corresponding to the radiator 26 in the radiation direction, respectively, and ventilate between the inside of the annular rotator 12 (setting area of the radiator 26) and the fan setting part 111.

Each of the fans 41 includes a fan axis 411 inclining rearward (Z2 shown in FIG. 3 and FIG. 5) with respect to the radiation direction around the body axis 121 (R1 direction shown in FIG. 2). The heat from the radiator 26 is sent to the duct 50 therebehind by rotating the fan 41 around the fan axis 411, and the heat is then exhausted to the outside from the exhaust port 163b via the duct 50. Since the heat from the radiator 26 is exhausted in this way, the inside of the annular rotator 12 has negative pressure. Thereby, the outside air is sucked to the radiators 26 from the aperture 15 side.

Since the fan 41 is arranged at positions separated by the position of the exhaust port 163b in the circumferential direction, it makes it possible for the noise form the fan 41 to be exhausted outside by not leaking the noise outside as it is but transmitting the noise along the circumferential direction in order to gradually reduce the noise.

It is acceptable for the angle of inclination of the fan axis 411 to be between 10 and 45 degrees. When the angle is set to be large, the effect to send out the heat from the radiator 26 to the rearward of the fan 41 is improved. On one hand, the front end parts of the fan 41 is caused to raise in the radiation direction, therefore, on the other hand, the space (fan setting part) for setting the fan 41 is extended in the radiation direction.

The fan 41 is arranged at the fan setting part 111 of the gantry 11, and the fan setting part 111 is covered with the side cover 165, therefore, the side cover 165 is needed to be extended in the radiation direction as wide as the width of the fan setting part 111 in the radiation direction. When the side cover 165 is extended in the radiation direction, the ceiling cover 164, which is smoothly continued to the side cover 165, is also needed to be extended in the radiation direction. When the ceiling cover 164 and the side cover 165 are extended in the radiation direction, the X-ray CT apparatus is extended in both the horizontal direction and the vertical direction.

When the X-ray CT apparatus is extended in both the horizontal direction and the vertical direction, it gives a feeling of pressure to the subject. The X-ray CT apparatus is designed to make the subject free from the feeling of pressure. For example, the ceiling cover 164 and the side covers 165 are inclined in the radiation direction (R1 direction) with respect to the rear direction (Z2 direction). The inclination angle of the cover 16 with respect to the Z2 direction is set to be α.

Provided that the subject stands at a specific position at the front side of the X-ray CT apparatus (in FIG. 3, the position away from the front cover 162 for a specific distance in the Z1 direction), the direction of a visual line VL viewing from the subject at the ceiling cover 164 and the side covers 165 is inclined in the radiation direction (R1 direction) around the body axis 121 with respect to the rear direction (Z2 direction). Here, the "specific length" means a distance form the front cover 162 to the subject when the subject stands at the front side of the X-ray CT apparatus for using the couch 70.

The inclination angle of the visual line VL with respect to the Z2 direction is set to be β. The inclination angle α of the cover 16 and the inclination angle β of the visual line VL will be expressed by a following formula (1):

$$\alpha \leq \beta \quad (1)$$

As shown above, by letting the inclination angle α of the cover 16 be less than or equal to the inclination angle β of the visual line VL, it is possible for the capacity of the X-ray CT apparatus to be large without giving a feeling of pressure to the subject.

Since the side cover 165 is inclined in the radiation direction with respect to the rear direction, the space between the fan setting part 111 and the side cover 165 (space in the radiation direction) becomes narrow in the front position and becomes wide in the rear position.

Here, in FIG. 3, the angle inclining the fan axis 411 of the fan 41 arranged at the front position rearwardly is indicated by θ1, and the angle inclining the fan axis 411 of the fan 41 arranged at the rear position rearwardly is indicated by θ2. It is preferable for the angle θ1 to be between 15 and 25 degrees. Also, it is preferable for the angle θ2 to be between 30 and 40 degrees.

It is more preferable for the angle θ1 to be about 20 degrees, and for the angle θ2 to be about 35 degrees.

The heat from the radiator 26 is sent obliquely in the radiation direction (R1 direction) with respect to the rear direction from the fan 41 arranged in the front position. The heat sent obliquely in the radiation direction with respect to the rear direction is reflected by the side cover 165, and then sent obliquely in the centripetal direction (R2 direction) with respect to the rear direction. The heat sent to the centripetal direction with respect to the rear direction (Z2 direction) is sent to the duct 50 arranged at the rearward of the fan 41. That is, it is possible for the fan 41 to send the heat from the radiator 26 to the duct 50 arranged therebehind.

It has been described the X-ray CT apparatus which has, in order not to give a feeling of pressure to the subject, a space between the fan setting part 111 and the side cover 165, which extends rearward, and the two fans 41 arranged at both the front and the rear of the space, respectively. Therefore, the side cover 165 has been inclined obliquely in the radiation direction with respect to the rear direction.

Without limiting to this case, for example, the X-ray CT apparatus may be configured such that when the visual line VL and the front cover 162 come into contact with each other at a contact 164a (see FIG. 3), the ceiling cover 164 and the side covers 165 are formed not to protrude from the present visual line VL in the radiation direction (R1 direction). Also, instead of inclining the ceiling cover 164 and the like, for example, the fan setting part 111 may be inclined obliquely in the centripetal direction with respect to the rear direction.

Figure 9:
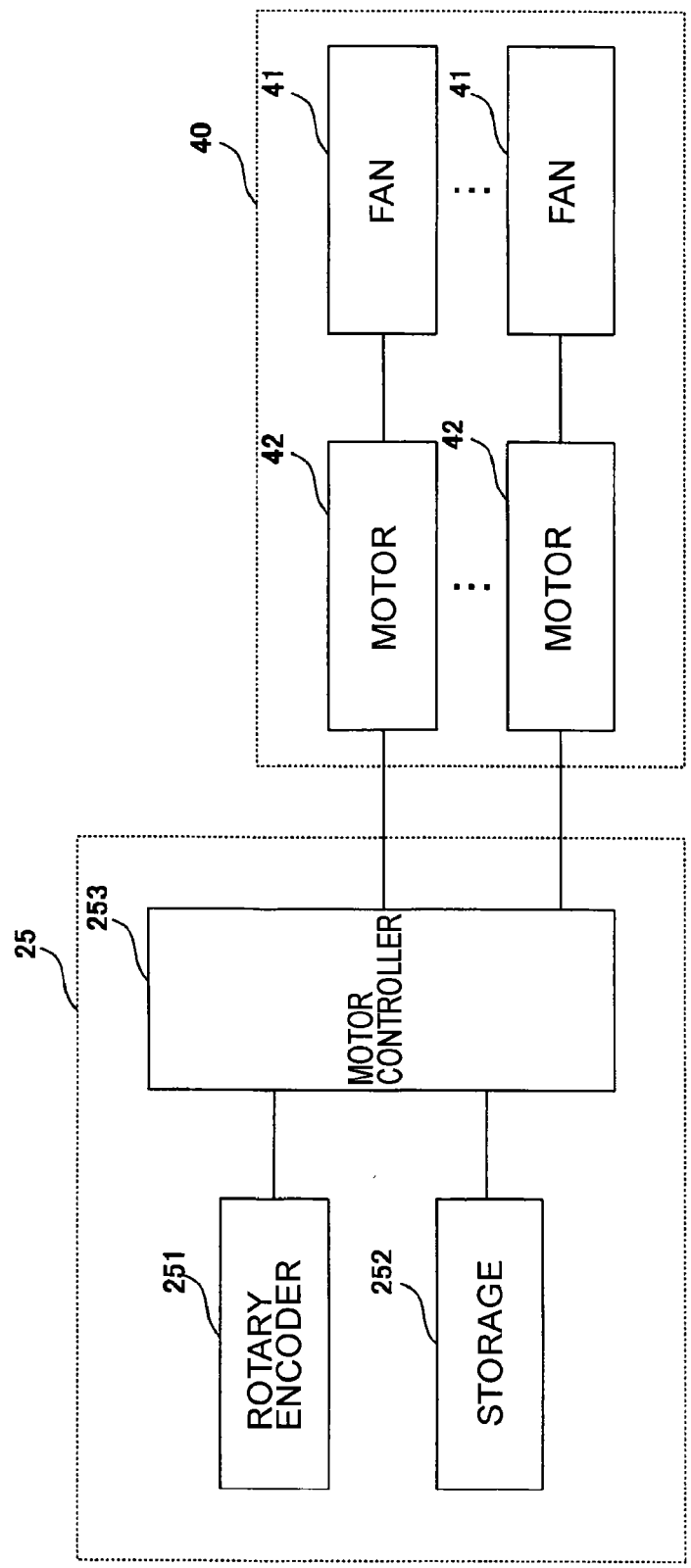
FIG. 9 is a block diagram of a gantry controller.

Next, the gantry controller 25 is described with reference to FIG. 2 and FIG. 9. FIG. 9 is a block diagram of the gantry controller 25 to mainly describe the control of the fan 41.

As shown in FIG. 9, the gantry controller 25 comprises a rotary encoder 251, a storage 252, and a motor controller 253.

The rotary encoder 251 encodes the amount of rotation (analog amount) of the annular rotator 12 into a number of pulses (digital amount).

The storage 252 stores the number of pulses corresponding to the rotating position of the annular rotator 12 (position at which the heat is radiated shown in FIG. 2) when the radiator 26 and the fan 41 are acting in the radiation direction.

The motor controller 253 receives the number of pulses from the rotary encoder 251, rotates the fan 41 when the received number is reached to the number of pulses corresponding to the position at which the heat is radiated, and controls motors 42 to stop the rotation of the fan 41 when the received number is not reached to the number of the pulses corresponding to the position at which the heat is radiated. Thereby, it is possible to exhaust the heat from the radiator 26 to the outside without fail, when the annular rotator 12 rotates to the position at which the heat is radiated.

(Duct)

Figure 10:
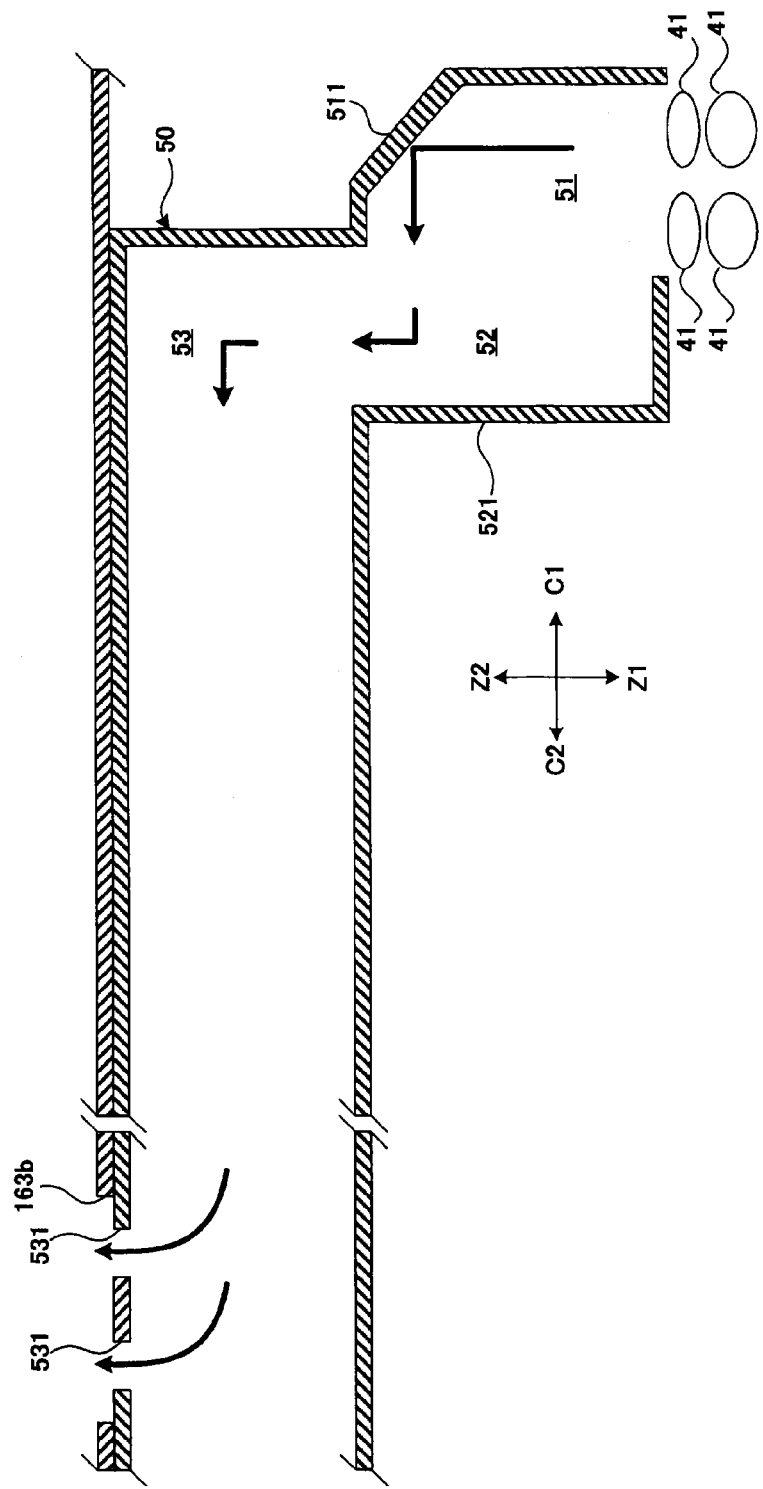
FIG. 10 is a cross-sectional view of a duct.

Next, the duct 50 is described with reference to FIG. 2, FIG. 3, FIG. 6, and FIG. 10. FIG. 10 is a cross-sectional view of the duct 50 taken along the circumferential direction.

As shown in FIG. 2, FIG. 3, FIG. 6, and FIG. 10, the duct 50 is provided between the frame 13 and the cover 16, and receives the exhaust air from the fan 41 at the rear position thereof to ventilate the air from the fan 41 to the exhaust port 163b.

The upstream end of the duct 50 is arranged at the position facing the fan 41. Further, the downstream end of the duct 50 is arranged at the position facing the exhaust port 163b. As shown in FIG. 6, the upstream ends are provided at both ends of the duct 50, and downstream side ports 531 are provided at the center part thereof, thereby being shared with the two coolers.

Some parts (bottom part and wall part) of the duct 50 are configured with the frame 13. The other parts thereof (ceiling part) are configured with some of the parts of the side covers 165. By configuring some parts of the duct 50 with the frame 13 and the other parts with the side covers 165, it is possible for the duct 50 to be manufactured independently without being installed to the frame 13, thereby reducing the manufacturing cost as well as the assembling cost.

In addition, the entire duct 50 may be configured with the frame 13 and/or the cover 16. It may also be possible to increase strength of the frame 13 and/or the cover 16 by letting the duct 50 have functions of the frame 13 and/or the cover 16.

As shown in FIG. 10, the duct 50 comprises a first path 51, an intermediate path 52, and a second path 53, and thereby forming a non-linear path.

At the downstream end of the first path 51, a wall 511 is provided. The wall 511 is formed to incline in the direction of the intermediate path 52 (C2 direction) with respect to the frontward direction of the first path 51 (Z1 direction).

The downstream end of the intermediate path 52 is extended to the anticlockwise direction (C2 direction), and provided with a wall 521. The downstream end of the intermediate path 52 and the upstream end of the second path 53 are ventilated in the front-rear direction.

The downstream end of the second path 53 is extended in the C2 direction, and has downstream side ports 531. The downstream side ports 531 are arranged to face the exhaust port 163b.

The sound from the fan 41 firstly passes through the first path 51 in the rearward direction (Z2 direction), then hits the wall 511 of the first path 51, and therefore, changes its travelling direction to C2 direction. Further, the sound hit the wall 521 of the intermediate path 52, and changes its travelling direction back to the rearward direction (Z2 direction). The sound then passes through the second path 53 in the C2 direction, and is exhausted to the outside from the exhaust port 163b via the downstream side ports 531 of the second path 53. That is, since the sound from the fan 41 hits the walls 511 and 521, one after another, the strength of the reflected sound is reduced so that it is possible to reduce the noise from the fan 41.

In addition, since the duct 50 is a path connecting the position the fan 41 is arranged (position of 1 o'clock shown in FIG. 2) and the position the exhaust port 163b is arranged (position of 12 o'clock shown in FIG. 5) and the fan 41 is arranged at the position, separating from the position the exhaust port 163b is arranged, in the circumferential direction, it is possible for the length of the path (duct length) not to be unnecessarily long, as well as preventing increase in size of the apparatus.

Hereinabove, it has been described a soundproof structure to reduce the noise from the fan 41 by providing the duct 50 at the rearward of the fan 41 (Z2 direction) and inclining the fan axis 411 of the fan 41 rearwardly.

[Other Soundproof Structure]

Next, other soundproof structure to reduce the noise from the inside of the cover 16 is described.

Figure 11:
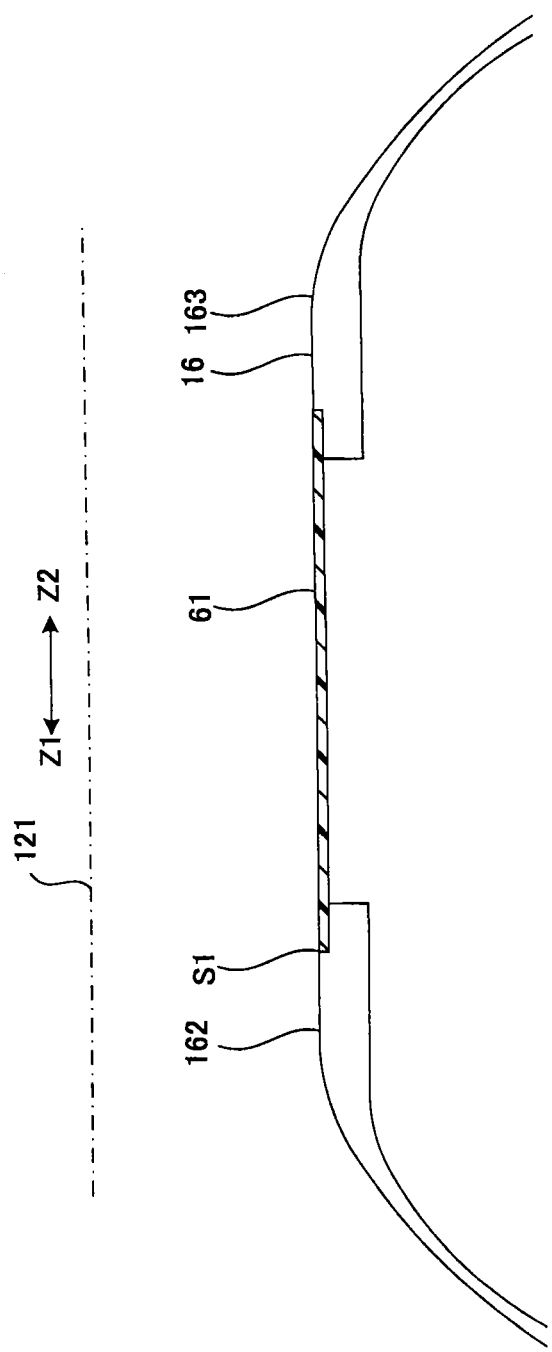
FIG. 11 is a cross-sectional view of a soundproof member arranged to close an X-ray transmission port.

Firstly, a soundproof structure configured with one soundproof member is described with reference to FIG. 11. FIG. 11 is a cross-sectional view of the soundproof structure configured with one soundproof member. The cross-sectional view of the FIG. 11 shows the aperture 15 taken along the rostrocaudal axis (Z-axis direction).

As shown in FIG. 11, an X-ray transmission port S1 for transmitting X-rays is formed between a rear end 162b of the cylinder-opening front part 162a of the front cover 162 and a front end 163b of the cylinder-opening rear part 163a of the rear cover 163. The width of the X-ray transmission port S1 in the circumferential direction is the size corresponding to the fan angle of beam X-rays. Also, the width of the X-ray transmission port S1 in the Z-axis direction is the size corresponding to the corn angle of beam X-rays.

As shown in FIG. 11, the X-ray transmission port S1 is closed with a sheet-like soundproof member 61. Thereby, it makes it possible to ensure the safety of the subject so that the subject does not touch the annular rotator 12. It makes it also possible to prevent blood and contrast agents from entrance into the inside of the annular rotator 12. In addition, it makes it possible to prevent the noise generated inside the cover 16 from leakage to the outside.

(Relationship Between Thickness of Soundproof Member and Sound Transmission Loss Value)

Figure 12:
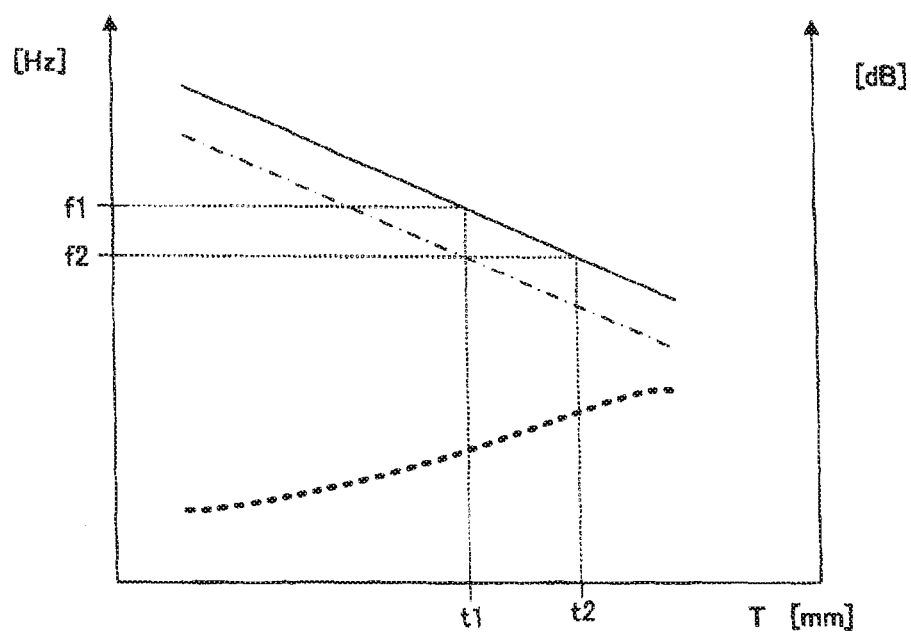
FIG. 12 is a diagram showing a relationship between the thickness of the soundproof member and a sound transmission loss value.

Here, a relationship between the thickness of the soundproof member 61 and a sound transmission loss value is described with reference to FIG. 12. FIG. 12 is a diagram showing the relationship between the thickness of the soundproof member and the sound transmission loss value. Here, the sound transmission loss value is the amount ten times the logarithm of the reciprocal of a sound transmission rate, and represented by decibels [dB]. Further, the sound transmission rate is a ratio of the transmitted sound intensity to the incident sound intensity.

In FIG. 12, the horizontal axis indicates the thickness [mm] of the soundproof member, and the vertical axis indicates a frequency [Hz] at which coincidence effect occurs as well as the sound transmission loss value. Here, the coincidence effect is a phenomenon in which the sound transmission loss value is reduced at a specific frequency.

Further, in FIG. 12, a frequency at which the coincidence effect occurs with respect to a thickness T of the soundproof member 61 when a soundproof layer 62 is not provided is indicated by a solid line, a frequency at which the coincidence effect occurs with respect to the thickness T of the soundproof member 61 when the soundproof layer 62 is provided is indicated by a dashed-dotted line, and a sound transmission loss value with respect to the thickness T of the soundproof member 61 is indicated by a broken line.

As the thickness T of the soundproof member 61 is increased, the sound transmission loss value becomes higher to improve a sound insulating property. Also, as the thickness T of the soundproof member 61 is increased, the frequency at which the coincidence effect occurs is shifted to the low-pitched sound side. The frequency at which the thickness T is t1 is indicated by f1 in FIG. 12. However, depending on frequency properties of noise, thickening of the thickness T dose not always cause the improvement of the sound insulating property. For example, if the frequency f1 is included in the noise, the coincidences effect occurs to reduce the sound transmission loss value as well as the sound insulting property. Therefore, it is needed for the thickness T of the soundproof member 61 to be thinner than the upper limit value t1 (T<t1).

Hereinabove, it has been described the soundproof structure configured with the soundproof member 61 only. Thereby, it made it clear that it was difficult to improve the sound insulating property using only the soundproof member 61.

(Soundproof Structure Between Cover and Floor Surface)

Figure 13:
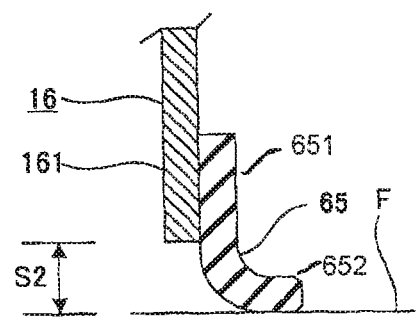
FIG. 13 is a cross-sectional view of an elastic member arranged to close a space between a floor surface and a cover.

Next, an elastic member 65 is described with reference to FIG. 1, FIG. 3, and FIG. 13. FIG. 13 is a cross-sectional view of the elastic member arranged to close a space S2 between the floor surface and the cover 16.

As shown in FIG. 1, FIG. 3 and FIG. 13, the space S2 is provided between the X-ray CT apparatus setting place (floor surface F) and the lower edge of the bottom cover 161. The space S2 has variance. The variance is due to product precision and assembling precision of the cover 16, therefore, it is difficult to completely eliminate the space S2. Through the space S2, the noise generated from the inside of the cover 16 is leaked to the outside. Meanwhile, if the lower edge of the bottom cover 161 is contacted to the floor surface F, abnormal noise is generated due to the vibration of the apparatus at the time of operation.

The elastic member 65 is formed in a belt-like shape with materials having elasticity (for example, resin rubber). One side edge 651 of the elastic member 65 is mounted along the lower edge of the bottom cover 161. Since the other side edge 652 of the elastic member 65 is contacted to the floor surface F and bent inward of the bottom cover 161, the elastic member 65 is elastically contacted to the floor part F with its restoring force. Thereby, it is possible to completely eliminate the space S2.

Closing the space S2 with the elastic member 65 makes it possible to reduce the noise generated from the inside of the cover 16. Also, since the side edge of the elastic member 65 is elastically contacted to the floor surface F, the abnormal noise is not generated by the vibration of the apparatus at the time of operation.

The other side edge 652 of the elastic member 65 is formed so as to bent inward of the bottom cover 161. Since the other side edge 652 of the elastic member 65 is hidden inside of the bottom cover 161, it is possible to improve appearance quality of the apparatus.

Further, the other side edge 652 of the elastic member 65 is curved toward the inside of the bottom cover 161 in advance so as to bend thereto. In order to be bent easily, the plate thickness of the other side edge 652 is made thinner than that of the other parts including the side edge 651.

[Second Embodiment]

Figure 14:
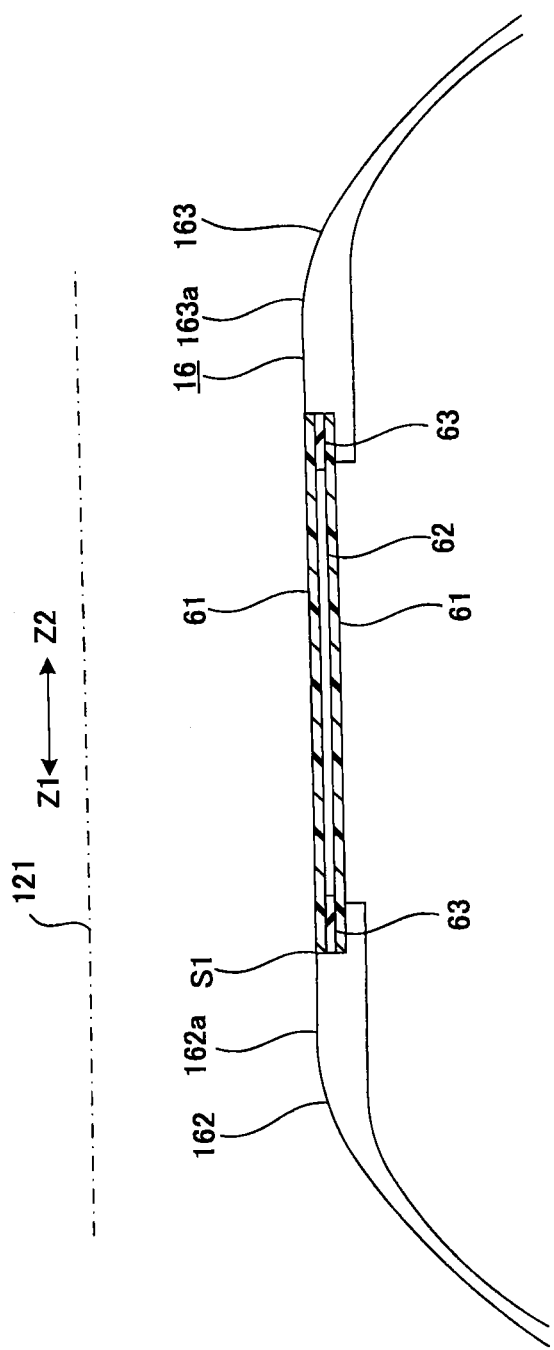
FIG. 14 is a cross-sectional view of a soundproof member arranged to close an X-ray transmission port in a second embodiment.

Next, a soundproof structure according to a second embodiment is described with reference to FIG. 14 and FIG. 15. FIG. 14 is a cross-sectional view of a soundproof structure provided with a soundproof layer. In FIG. 14 shows the cross-sectional view of the aperture 15 taken along the rostrocaudal direction (Z-axis direction).

In the second embodiment, descriptions for the same configurations as the first embodiment are omitted and the different configurations are mainly described.

As shown in FIG. 14, the soundproof structure according to the present embodiment comprises two of the soundproof member 61 and the soundproof layer 62. It makes it possible to improve the sound insulating property. The soundproof layer 62 is configured with an air layer. Two or more of combination of two of the soundproof member 61 and the soundproof layer 62 may be arranged. Further, the soundproof layer 62 may be configured with a sound absorbing member and/or a sound reflecting member.

Figure 15:
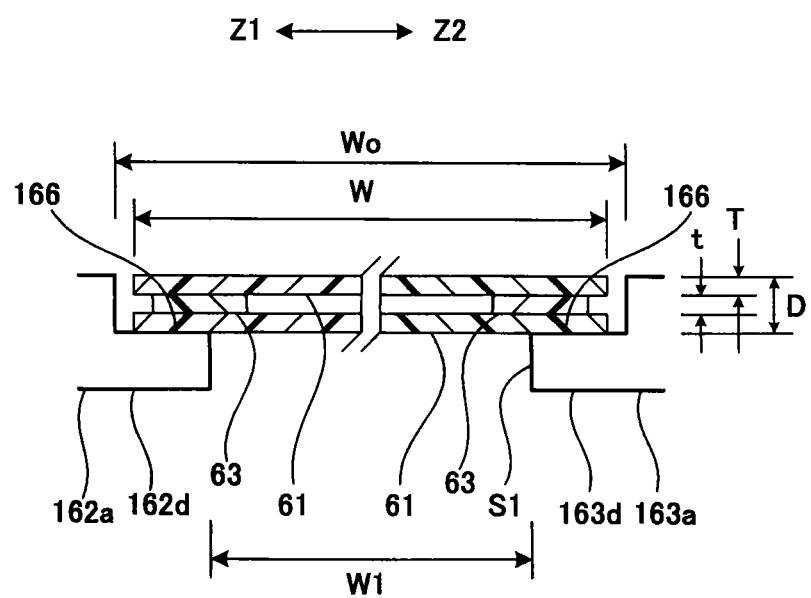
FIG. 15 is a partially enlarged cross-sectional view of the soundproof member.

FIG. 15 is a partially enlarged cross-sectional view of the soundproof member. As shown in FIG. 14 and FIG. 15, as the soundproof structure, two of the soundproof member 61 are arranged so as to sandwich the air layer as the soundproof layer 62. Those two soundproof members 61 are provided to bridge over the X-ray transmission port S1. FIG. 14 and FIG. 15 show that those two soundproof members 61 are arranged in parallel, however, the arrangement is not limited to this, and those two soundproof members 61 may be arranged to form a specific angel.

(Soundproof Member)

The soundproof member 61 is a material having a large sound transmission loss, and configured from a thin film-like material having a good transmittance with respect to a laser for X-rays and marking. Thereby, it is possible to suppress the deterioration in the image quality of images obtained by the X-ray imaging.

A variety of the soundproof members 61 include a sound absorbing member in which a part of the acoustic energy is converted to heat energy to deaden a reflected sound, and a sound reflecting member having properties of reflecting and refracting an incident sound.

As examples of the sound absorbing member, a fiber-like and a sponge-like members having small holes therein are used, and it is preferable that, as a representative example of the material used for the sound absorbing member, a porous material, such as glass wool and urethane, is used.

The sound reflecting member, for example, may be configured by encapsulating gas, such as helium having acoustic velocity greater than that of air, into between the two soundproof members.

In the present embodiment, as the soundproof member 61, for example, polyethylene terephthalate (PET) is used. It is preferable to use Mylar (registered trademark) as the PET. It is also preferable that the thickness of the soundproof member 61 is between 0.5 [mm] and 1.0 [mm].

(Air Layer)

As described above, the air layer as the soundproof layer 62 is sandwiched between two of the soundproof member 61. The air layer may be formed by sticking together those two soundproof members 61 by a double-sided tape 63 having a thickness between 0.5 [mm] and 1.0 [mm].

It is possible to improve the sound insulating property by providing the air layer. Further, thickening the air layer makes lowering the frequency at which the coincident effect occurs. The frequency lowered by providing the air layer is indicated by f2 in FIG. 12. In FIG. 12, the upper limit value of the thickness T of the soundproof member 61 with respect to the frequency f2 is indicated by t2. As shown in FIG. 12, by increasing the upper limit value of the thickness T of the soundproof member 61 to t2, it is possible that the thickness T of the soundproof member 61 is increased (T<t2), the sound transmission loss value is enhanced, and the sound insulating property is improved.

As shown in FIG. 14 and FIG. 15, a step 166 is formed at the rear end 162d of the cylinder-opening front part 162a. Similarly, another step 166 is formed at the front end 163d of the cylinder-opening rear part 163a. When the depth of each of the step 166 is assumed as D and the thickness of the double-sided tape 63 is assumed as t, a relationship between those is expressed by the following formula (2):

$$D \geq 2T + t \quad (2)$$

Also, when the length of the double-sided tape 63 is assumed as W, the width between those two steps 166 is assumed as W0, and the width of the X-ray transmission port S1 in the Z-axis direction is assumed as W1, a relationship between those is expressed by the following formula (3):

$$W0 \geq W > W1 \quad (3)$$

By stacking the two soundproof members 61 together, it is possible to improve the sound insulating effect. It is also possible to improve the sound insulating property from the low-pitched tone to the intermediate-pitched tone due to the effectiveness of the air layer thickness.

By utilizing the double-sided tape 63, airtightness of the air layer is improved; therefore, the improvement of the sound insulating property can be realized.

The thickness of the air layer may be changed by changing the plate thickness of the double-sided tape 63. Thereby, the frequency is set to be less than or equal to the specified frequency at which the coincidence effect occurs. Also, two of the soundproof member 61 may be arranged so as to form a specific angle therebetween. In this case, the plate thickness of the double-sided tape 63 may be different between at the rear end 162d side of the cylinder-opening front part 162a and at the front end 163d side of the cylinder-opening rear part 163a.

Now, it is described an operation procedure to close the X-ray transmission port S1 using the soundproof members 61.

Firstly, an adhesive agent is applied to the step 166. One of the soundproof members 61 is then stuck to the step 166 with the agent.

Next, on one side of the double-sided tape 63, the aforementioned soundproof member 61 is stuck. Another soundproof member 61 is then stuck on the other side of the double-sided tape 63.

By the above-mentioned work, the X-ray transmission port S1 can be closed using the soundproof members 61. Further, by utilizing the double-sided tape 63, two of the soundproof member 61 can be easily stuck together, and it makes is possible to improve workability.

The two sound absorbing members 61 stuck together with the double-sided tape 63 may be stuck to the step 166. It may also be possible that the double-sided tape 63 is stuck to the step 166 and one of the soundproof members 61 is then stuck onto the double-sided tape 63.

[Third Embodiment]

Figure 16:
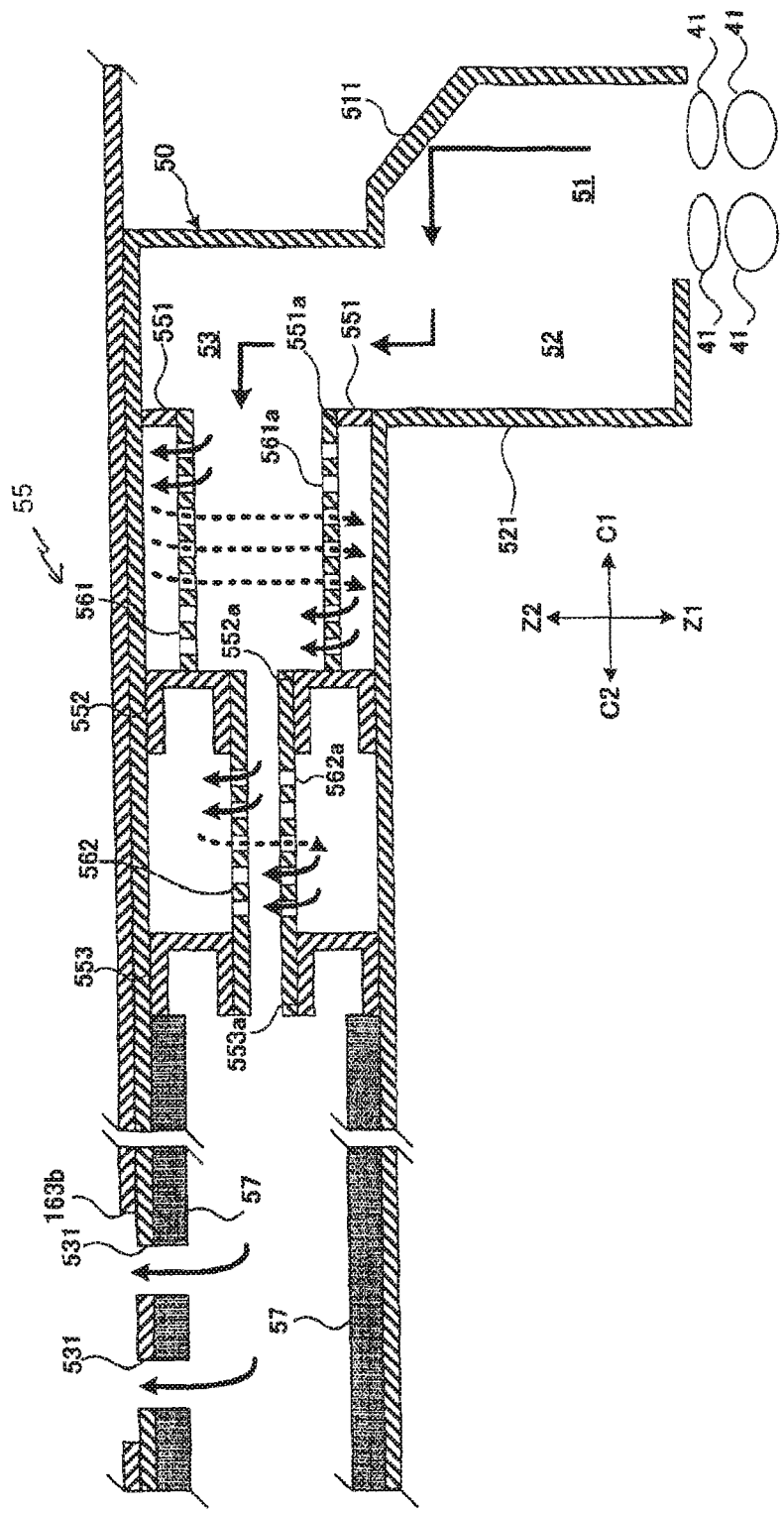
FIG. 16 is a cross-sectional view of a duct in a third embodiment.

Next, a soundproof structure according to a third embodiment is described with reference to FIG. 16. FIG. 16 is a cross-sectional view of the soundproof structure. FIG. 16 shows a baffle 55 and sound absorbing members 57 provided in the duct 50.

FIG. 16 shows the first path 51, the intermediate path 52, and the second path 53 as a cross-sectional view taken along the outer circumference of the annular rotator 12.

In the third embodiment, descriptions for the same configurations as the first embodiment are omitted and the different configurations are mainly described.

In the first embodiment, the soundproof structure in which the duct 50 is formed as a non-linear path is described. Whereas, in the third embodiment, the soundproof structure in which the baffle 55 and the sound absorbing members 57 are provided in the duct 50 is described.

(Baffle)

As shown in FIG. 16, in the second path 53, the baffle 55 is provided in order to reduce the noise from the fan 41 by complicating the path.

The baffle 55 comprises first partition members 551, second partition members 552, third partition members 553, fourth partition members, first tubular members 561, and second tubular members 562, These members may he formed by the same materials as the duct 50.

The first partition members 551 partition the second path 53 into the upstream side and the downstream side, and each of the members has a hole 551a having a radius R1 in the middle. The second partition members 552 are arranged downstream of the first partition member 551, to partition the second path 53 into the upstream side and the downstream side, and each of the members has a hole 552a having a radius R2 in the middle. The third partition members 553 are arranged downstream of the second partition member 552, to partition the second path 53 into the upstream side and the downstream side, and each of the members has a hole 553a having the radius R2 in the middle.

The first tubular member 561 is arranged to be sandwiched between the first partition member 551 and the second partition member 552, and has a tubular wall with multiple small openings 561a. The upstream side end of the first tubular member 561 is fitted to the hole 551a, and the downstream side end of the first tubular member 561 is abutted to the second partition member 552.

The second tubular member 562 is arranged to be sandwiched between the second partition member 552 and the third partition member 553, and has a tubular wall with multiple small openings 562a. The upstream side end of the second tubular member 562 is fitted to the hole 552a, and the downstream side end of the second tubular member 562 is fitted to the hole 553a.

The sound from the fan 41 is transmitted from the intermediate path 52 to the second path 53. A part of the sound is reflected by the first partition members 551. A part of the sound transmitted to the first tubular members 561 is reflected by the inner wall thereof. Other part of the sound is transmitted from the inside of the first tubular members 561 to the outside via the small openings 561a, reflected by the inner wall of the intermediate path 52, and back from the outside to the inside via the small openings 561a. In this way, since the sound from the fan 41 is reflected, it is possible that the strength of the reflected sound is decreased and the noise from the fan 41 is reduced.

The sound from the fan 41 is transmitted from the first tubular members 561 to the second tubular members 562. A part of the sound transmitted to the second tubular members 562 is reflected by the inner wall thereof. Other part of the sound is transmitted from the inside of the second tubular members 562 to the outside via the small openings 562a, reflected by the inner wall of the second path 53, and back from the outside to the inside via the small openings 562a.

By reflecting the sound transmitted to the second tubular members 562, it is possible to further decrease the strength of the reflected sound, and further reduce the noise from the fan 41. The noise which is reduced in this way is exhausted from the exhaust port 163b to the outside.

(Sound Absorbing Member)

In order to further reduce the noise from the fan 41 by passing through the second tubular members 562 of the baffle 55, the sound absorbing members 57 are provided.

As shown in FIG. 16, the sound absorbing members 57 are arranged downstream of the third partition members 553. The sound absorbing members 57 are installed the inner wall of the second path 53, respectively.

The noise from the fan 41 is reduced by hitting the sound absorbing members 57, and then exhausted to the outside from the exhaust port 163b. It is therefore possible to further reduce the noise from the fan 41.

In the third embodiment, by providing the baffle 55 and the sound absorbing members 57, it is possible to reduce the sound transmitting to the exhaust port 163b through the duct 50.

In the present embodiment, a sound absorbing member may be installed to the inner surface of the cover 16. As an example of the sound absorbing member, a porous material, such as rock wool and glass wool, in a form of high-density plate is used. It is preferable to use a thin film, such as polyether and vinyl film, as an example of the porous material.

Further, in the present embodiment, a sound reflecting member having properties of reflecting and refracting an incident sound may be installed to the inner surface of the cover 16.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

EXPLANATION OF SYMBOLS

P Subject
S1 X-ray transmission port
S2 Space
10 X-ray CT apparatus
11 Gantry
111 Fan setting part
112 Communication port
12 Annular rotator
121 Body axis
122 Vent hole
13 Frame
14 Rotating mechanism
15 Aperture
16 Cover
161 Bottom cover
162 Front cover
162a Cylinder-opening front part
163 Rear cover
163a Cylinder-opening rear part 163b Exhaust port
164 Ceiling cover
164a Contact
165 Side cover
166 Step
17 X-ray tube
18 X-ray detector
19 Data acquisition system (DAS)
20 Data transmitter
21 Console
22 Slip ring
23 Fixed part
24 X-ray controller
25 Gantry controller
26 Radiator
31 Preprocessor
32 Bus line
33 System controller
34 Input device
35 Data storage
36 Reconstruction processor
37 Data processor
38 Display
39 High voltage generator
40 Cooler
41 Fan
411 Fan axis
50 Duct
51 First path
511 Wall
52 Intermediate path
521 Wall
53 Second path
531 Downstream side port
55 Baffle
551 First partition member
552 Second partition member
553 Third partition member
561 First tubular member
562 Second tubular member
57 Sound absorbing member
61 Soundproof member
62 Soundproof layer
63 Double-sided tape
65 Elastic member
70 Couch
71 Top

The invention claimed is:

1. An X-ray CT apparatus, comprising:
an annular rotator having an X-ray tube and radiators configured to exhaust heat from the X-ray tube, and having an aperture to which a couch is insertable from a front of the rotator to the center of the rotator,
a gantry having a frame arranged rearward of the annular rotator, and configured to support the annular rotator to allow the annular rotator to rotate around a body axis,
a cover configured to cover the annular rotator and the gantry, and having exhaust ports,
a cooler arranged at a position between an outer peripheral surface of the annular rotator and the cover, the cooler having a fan arranged on the gantry, and
a duct, arranged between the frame and the cover, and configured to receive the exhaust air from the fan, at rearward of the gantry, to exhaust the air from the fan to the exhaust ports, wherein
the fan has a fan axis, and is configured to send the exhausted heat to the duct by rotating around the fan axis.

2. The X-ray CT apparatus according to claim 1, wherein the radiators are arranged in a circumferential direction of the annular rotator with the X-ray tube therebetween, and
two of the coolers are symmetrically arranged at positions corresponding to two of the radiators, respectively, when the annular rotator is rotated so that a position of the X-ray tube corresponds to the positions of exhaust ports.

3. The X-ray CT apparatus according to claim 1, wherein the cooler comprises two fans, and
the two fans are arranged at the front of the rotator and a rear of the rotator, respectively.

4. The X-ray CT apparatus according to claim 1, wherein an angle to incline the fan axis rearwardly with respect to a radial direction is between 10 and 45 degrees.

5. The X-ray CT apparatus according to claim 3, wherein the fans are arranged at a space between the outer peripheral surface of the annular rotator and the cover, the space expanding toward a rear of the rotator,
the fan axis of the fan arranged at the front position is inclined rearwardly with respect to a radial direction at an angle between 15 and 25 degrees, and
the fan axis of the fan arranged at the rear position is inclined rearwardly with respect to the radial direction at an angle between 30 and 40 degrees.

6. The X-ray CT apparatus according to claim 1, wherein the duct is connected with the frame.

7. The X-ray CT apparatus according to claim 1, further comprising:
a soundproof structure configured to reduce a sound transmitting to the exhaust ports through the duct.

8. The X-ray CT apparatus according to claim 7, wherein the soundproof structure is configured by forming a non-linear path in the duct.

9. The X-ray CT apparatus according to claim 8, wherein the duct comprises a first path extending from one end thereof arranged at a position facing the fan, and a second path extending to the exhaust ports along a circumferential direction of the annular rotator from the other end of the first path.

10. The X-ray CT apparatus according to claim 1, wherein a sound absorbing member is installed at an inner wall of the cover.

11. The X-ray CT apparatus according to claim 1, wherein a sound reflecting member is installed at an inner wall of the cover.

12. The X-ray CT apparatus according to claim 2, wherein the cooler comprises two fans, and
the two fans are arranged at the front of the rotator and a rear of the rotator, respectively.

13. The X-ray CT apparatus according to claim 2, wherein an angle to incline the fan axis rearwardly with respect to a radial direction is between 10 and 45 degrees.

14. The X-ray CT apparatus according to claim 3, wherein an angle to incline the fan axis rearwardly with respect to a radial direction is between 10 and 45 degrees.

15. The X-ray CT apparatus according to claim 12, wherein
the fans are arranged at a space between the outer peripheral surface of the annular rotator and the cover, the space expanding toward a rear of the rotator, the fan axis of the fan arranged at the front position is inclined rearwardly with respect to the radial direction at an angle between 15 and 25 degrees, and the fan axis of the fan arranged at the rear position is inclined rearwardly with respect to the radial direction at an angle between 30 and 40 degrees.

16. The X-ray CT apparatus according to claim 6, further comprising:

a soundproof structure configured to reduce a sound transmitting to the exhaust ports through the duct.

17. The X-ray CT apparatus according to claim 1, wherein the cooler is arranged along a circumferential direction of the annular rotator at a position away from positions of the exhaust ports.

18. The X-ray CT apparatus according to claim 1, wherein the fan axis inclines rearward with respect to a radial direction around the body axis.

19. The X-ray CT apparatus according to claim 1, wherein the cooler is arranged along a circumferential direction of the annular rotator at a position away from positions of the exhaust ports, and the duct comprises a first path extending from one end thereof arranged at a position facing the fan, and a second path extending to the exhaust ports along a circumferential direction of the annular rotator from the other end of the first path.

\* \* \* \* \*